United States Patent
Cosby

(12) 
(10) Patent No.: US 12,150,887 B2
(45) Date of Patent: Nov. 26, 2024

(54) STRAP-ON CONDOM ASSEMBLY

(71) Applicant: Robert Cosby, Indianapolis, IN (US)

(72) Inventor: Robert Cosby, Indianapolis, IN (US)

( * ) Notice: Subject to any disclaimer, the term of this patent is extended or adjusted under 35 U.S.C. 154(b) by 349 days.

(21) Appl. No.: 17/580,225

(22) Filed: Jan. 20, 2022

(65) Prior Publication Data
US 2023/0277368 A1  Sep. 7, 2023

(51) Int. Cl.
*A61F 6/04* (2006.01)

(52) U.S. Cl.
CPC .......... *A61F 6/04* (2013.01); *A61F 2006/047* (2013.01)

(58) Field of Classification Search
CPC .................. A61F 6/04; A61F 2006/047; A61F 2006/041; A61F 6/065; A61F 6/20; A61F 6/02; Y10S 128/918
See application file for complete search history.

(56) References Cited

U.S. PATENT DOCUMENTS

| | | |
|---|---|---|
| 4,971,071 A | 11/1990 | Johnson |
| 5,351,699 A | 10/1994 | Hammons |
| 5,531,230 A | 7/1996 | Bell |
| 5,979,448 A | 11/1999 | Weller |
| 7,131,443 B2 | 11/2006 | Van Gaalen |
| D603,039 S | 10/2009 | Resnic |
| 10,226,377 B2 | 3/2019 | Buddharaju |
| 2006/0124135 A1* | 6/2006 | Mayfield .................. A61F 6/04 128/842 |

FOREIGN PATENT DOCUMENTS

WO   WO2017100633   6/2017

* cited by examiner

*Primary Examiner* — Ophelia A Hawthorne

(57) ABSTRACT

A strap-on condom assembly for inhibiting a condom from falling off during intercourse includes a condom that is wearable on a user's penis during intercourse to protect against the transmission of sexually transmitted diseases. A first strap is coupled to the condom and the first strap can be extended around the user's waist when the condom is being worn. A second strap is coupled to the condom and the second strap can be extended around the user's waist when the condom is being worn. The second strap is matable to the first strap to inhibit the condom from falling off of the user's penis during intercourse.

5 Claims, 4 Drawing Sheets

STRAP-ON CONDOM ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to condom devices and more particularly pertains to a new condom device for inhibiting a condom from falling off during intercourse. The device includes a condom and a pair of straps each coupled to and extending away from the condom in opposing directions from each other. The device includes a pair of mating members, each coupled to a respective one of the straps. Each of the mating members is matable to each other for retaining the straps around the user's waist thereby inhibiting the condom from falling off during intercourse.

(2) Description of Related Art Including Information Disclosed Under 37 CFR 1.97 and 1.98

The prior art relates to condom devices including a condom, being comprised of an electrically conductive material, and a pair of straps each coupled to the condom. The prior art discloses a condom, a belt that is wearable around a waist of a user and a pair of straps each coupled between the condom and the belt. The prior art discloses a condom which includes a pair of straps each extending away from the condom and a package in which the condom and straps are stored until use. The prior art discloses a condom retention device that includes a trough which is wearable around a condom when the condom is being worn, a strap coupled to the trough for extending around a user's waist and a fastener coupled to the trough which engages the strap. The prior art discloses a condom retainer that includes a pair of leg straps which are extendable around a user's legs and a loop through which a condom can be extended when the condom is being worn.

BRIEF SUMMARY OF THE INVENTION

An embodiment of the disclosure meets the needs presented above by generally comprising a condom that is wearable on a user's penis during intercourse to protect against the transmission of sexually transmitted diseases. A first strap is coupled to the condom and the first strap can be extended around the user's waist when the condom is being worn. A second strap is coupled to the condom and the second strap can be extended around the user's waist when the condom is being worn. The second strap is matable to the first strap to inhibit the condom from falling off of the user's penis during intercourse.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
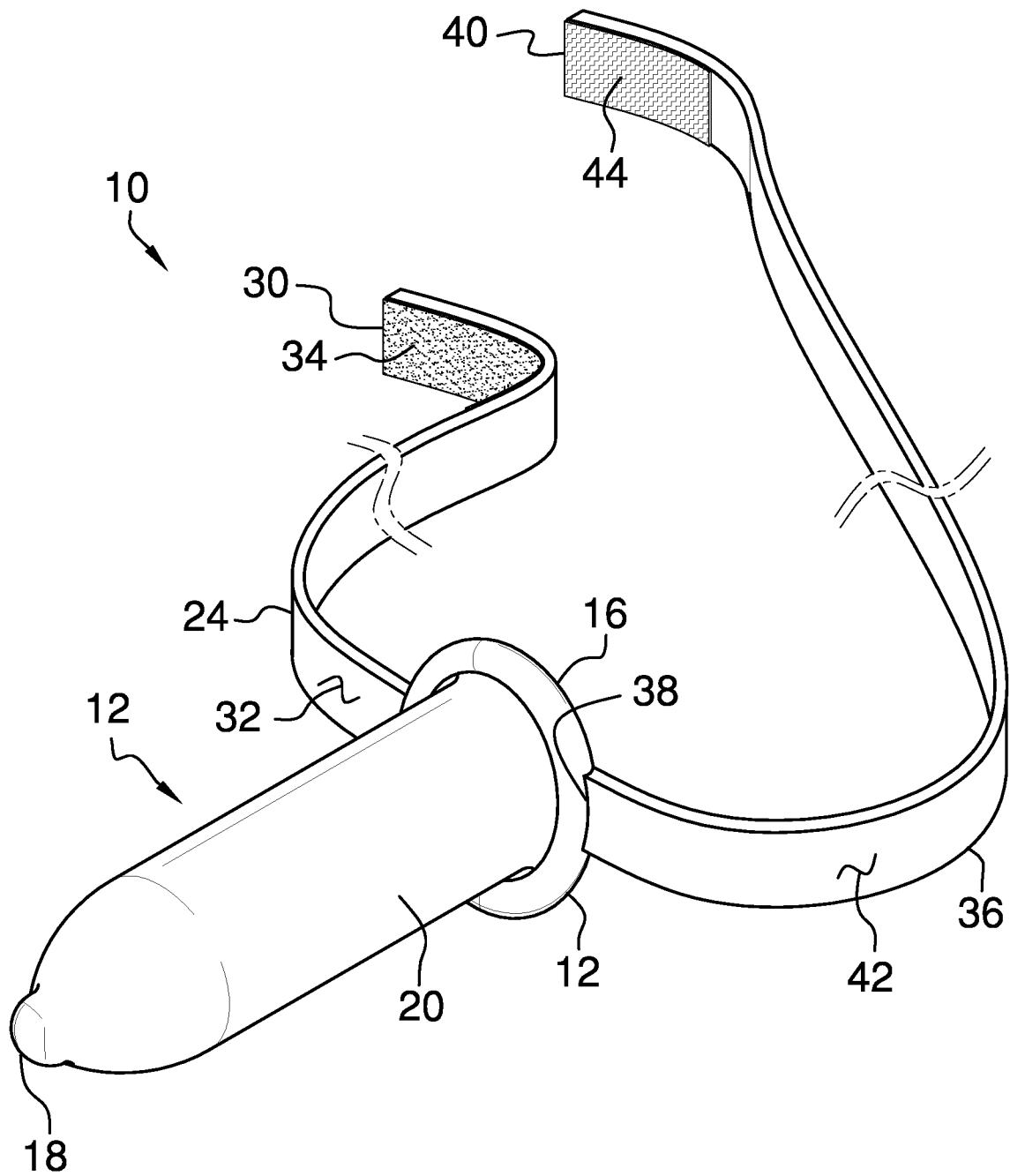
FIG. 1 is a perspective view of a strap-on condom assembly according to an embodiment of the disclosure.
Figure 2:
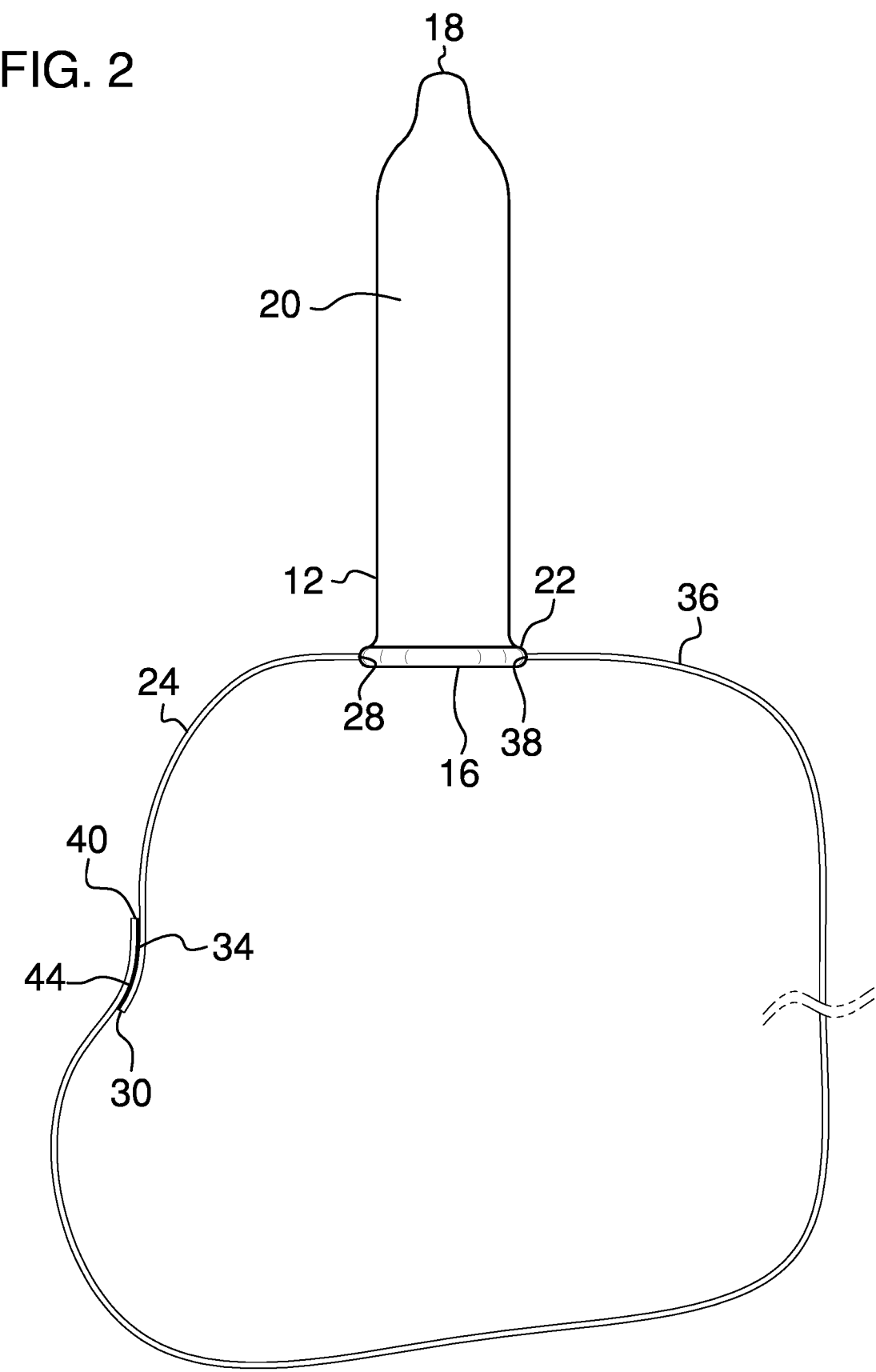
FIG. 2 is a top view of an embodiment of the disclosure.
Figure 3:
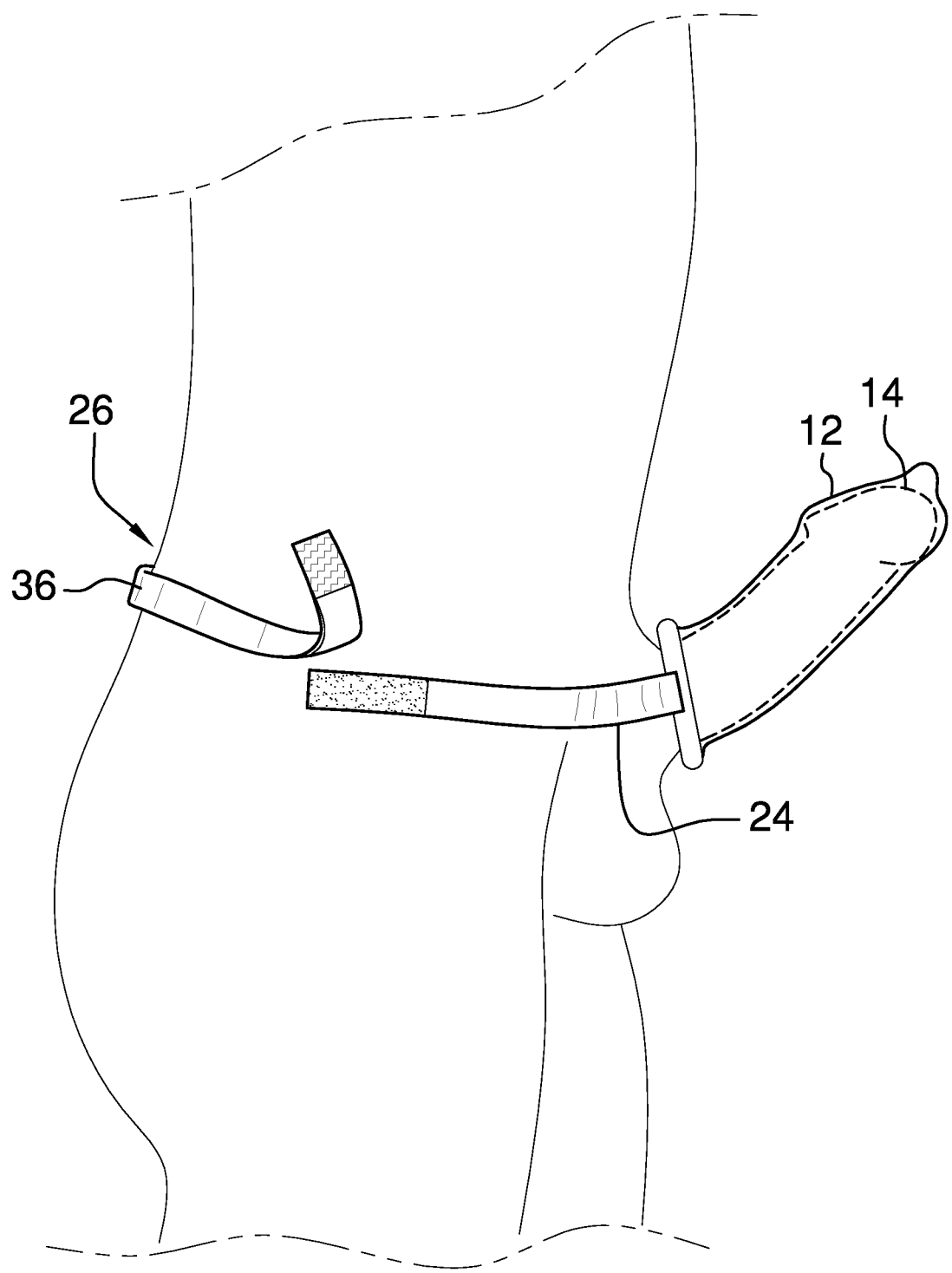
FIG. 3 is a perspective in-use view of an embodiment of the disclosure.
Figure 4:
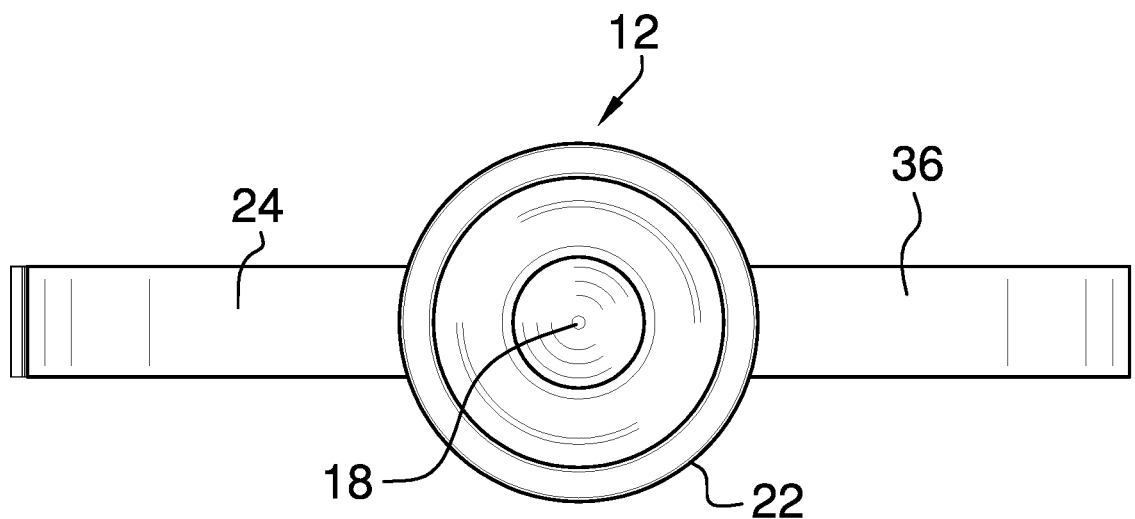
FIG. 4 is a front view of an embodiment of the disclosure.
Figure 5:
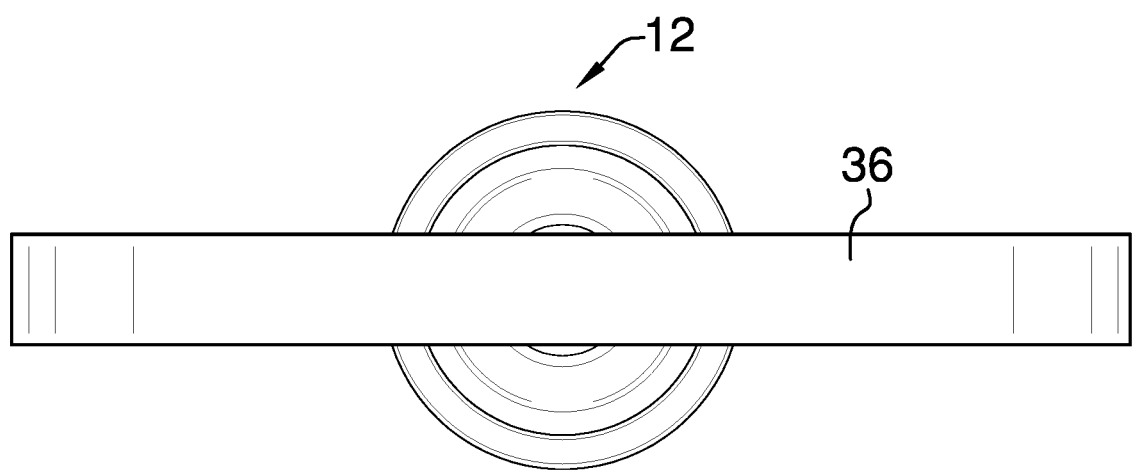
FIG. 5 is a back view of an embodiment of the disclosure.

With reference now to the drawings, and in particular to FIGS. 1 through 5 thereof, a new condom device embodying the principles and concepts of an embodiment of the disclosure and generally designated by the reference numeral 10 will be described.

As best illustrated in FIGS. 1 through 5, the strap-on condom assembly 10 generally comprises a condom 12 that is wearable on a user's penis 14 during intercourse to protect against the transmission of sexually transmitted diseases. The condom 12 has a first end 16, a second end 18 and an outer wall 20 extending between the first end 16 and the second end 18. The first end 16 is open, the second end 18 is closed and the condom 12 is elongated between the first end 16 and the second end 18. The condom 12 has a ring 22 extending around the outer wall 20 and the ring 22 is aligned with the first end 16. Furthermore, the condom 12 is comprised of a fluid impermeable material, including but not being limited to, latex or polyurethane, to inhibit bodily fluids from passing through the condom 12. The condom 12 may be a condom of any conventional design and the condom 12 may be manufactured in a variety of sizes for accommodating the anatomy of a variety of users.

A first strap 24 is coupled to the condom 12 and the first strap 24 can be extended around the user's waist 26 when the condom 12 is being worn. The first strap 24 has a primary end 28, a secondary end 30 and an outer surface 32 extending between the primary end 28 and the secondary end 30, and the primary end 28 is coupled to the ring 22 on the outer wall 20 of the condom 12. A first mating member 34 is provided and the first mating member 34 is coupled to the first strap 24. The first mating member 34 is positioned on the outer surface 32 and the first mating member 34 is positioned adjacent to the secondary end 30. Additionally, the first mating member 34 may comprise a hook and loop fastener or other type of releasable fastener.

A second strap 36 is coupled to the condom 12 and the second strap 36 can be extended around the user's waist 26 when the condom 12 is being worn. The second strap 36 has a primary end 38, a secondary end 40 and an outer surface 42 extending between the primary end 38 and the secondary end 40 of the second strap 36. The primary end 38 of the second strap 36 is coupled to the ring 22 on the outer wall 20 of the condom 12 and the second strap 36 is positioned on an opposing side of the ring 22 with respect to the first strap 24.

A second mating member 44 is coupled to the second strap 36 and the second mating member 44 is releasably matable to the first mating member 34 such that the first strap 24 and the second strap 36 form a closed loop. In this way the first strap 24 and the second strap 36 inhibit the condom 12 from falling off of the user's penis 14 during intercourse. The second mating member 44 is positioned on the outer surface 42 of the second strap 36 and the second mating member 44 is aligned with the secondary end 40 of the second strap 36. The second mating member 44 may comprise a hook and loop fastener or other type of fastener that is complementary to the first mating member 34. The second strap 36 has a length that is greater than the length of the first strap 24. In this way the first strap 24 and the second strap 36 meet each other on a side of the user's waist 26 when the first strap 24 and the second strap 36 are wrapped around the user's waist 26 to assist the user with mating the first strap 24 to the second strap 36.

In use, the condom 12 is worn on the user's penis 14 prior to engaging in sexual intercourse. The each of the first strap 24 and the second strap 36 are extended around the user's waist 26. Additionally, the first mating member 34 is attached to the second mating member 44 to form the first strap 24 and the second strap 36 into a closed loop. In this way the first strap 24 and the second strap 36 inhibit the condom 12 from falling off of the user's penis 14 during intercourse. The first strap 24 is removed uncoupled from the second strap 36 and the condom 12 is discarded after sexual intercourse is completed.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A strap-on condom assembly for inhibiting a condom from falling of a user during intercourse, said assembly comprising:
    a condom being wearable on a user's penis during intercourse wherein said condom is configured to protect against the transmission of sexually transmitted diseases;
    a first strap being coupled to said condom wherein said first strap is configured to be extended around the user's waist when said condom is being worn;
    a second strap being coupled to said condom wherein said second strap is configured to be extended around the user's waist when said condom is being worn, said second strap being matable to said first strap wherein said first strap and said second strap are configured to inhibit said condom from falling off of the user's penis during intercourse, said second strap having a length being greater than a length of said first strap;
    wherein said condom has a first end, a second end and an outer wall extending between said first end and said second end, said first end being open, said second end being closed, said condom being elongated between said first end and said second end, said condom having a ring extending around said outer wall, said ring being aligned with said first end, said condom being comprised of a fluid impermeable material wherein said condom is configured to inhibit bodily fluids from passing through said condom;
    wherein said first strap has a primary end being coupled directly to said ring of said condom on said outer wall of said condom; and
    wherein said second strap has a primary end being coupled directly to said ring of said condom on said outer wall of said condom, said second strap being positioned on an opposing side of said ring with respect to said first strap.

2. The assembly according to claim 1, wherein:
    said first strap has a primary end, a secondary end and an outer surface extending between said primary end and said secondary end; and
    said assembly includes a first mating member being coupled to said first strap, said first mating member being positioned on said outer surface, said first mating member being positioned adjacent to said secondary end.

3. The assembly according to claim 2, wherein:
    said second strap has a primary end, a secondary end and an outer surface extending between said primary end and said secondary end of said second strap, said primary end of said second strap being coupled to said ring on said outer wall of said condom, said second strap being positioned on an opposing side of said ring with respect to said first strap; and
    said assembly includes a second mating member being coupled to said second strap, said second mating member being positioned on said outer surface of said second strap, said second mating member being aligned with said secondary end of said second strap.

4. The assembly according to claim 3, wherein said second mating member is releasably matable to said first mating member such that said first strap and said second strap forms a closed loop wherein said first strap and said second strap are configured to inhibit said condom from falling off of the user's penis during intercourse.

5. A strap-on condom assembly for inhibiting a condom from falling of a user during intercourse, said assembly comprising:

a condom being wearable on a user's penis during intercourse wherein said condom is configured to protect against the transmission of sexually transmitted diseases, said condom having a first end, a second end and an outer wall extending between said first end and said second end, said first end being open, said second end being closed, said condom being elongated between said first end and said second end, said condom having a ring extending around said outer wall, said ring being aligned with said first end, said condom being comprised of a fluid impermeable material wherein said condom is configured to inhibit bodily fluids from passing through said condom;

a first strap being coupled directly to said condom wherein said first strap is configured to be extended around the user's waist when said condom is being worn, said first strap having a primary end, a secondary end and an outer surface extending between said primary end and said secondary end, said primary end being coupled directly to said ring on said outer wall of said condom;

a first mating member being coupled to said first strap, said first mating member being positioned on said outer surface, said first mating member being positioned adjacent to said secondary end;

a second strap being coupled directly to said condom wherein said second strap is configured to be extended around the user's waist when said condom is being worn, said second strap having a primary end, a secondary end and an outer surface extending between said primary end and said secondary end of said second strap, said primary end of said second strap being coupled directly to said ring on said outer wall of said condom, said second strap being positioned on an opposing side of said ring with respect to said first strap, said second strap having a length being greater than a length of said first strap; and a second mating member being coupled to said second strap, said second mating member being releasably matable to said first mating member such that said first strap and said second strap forms a closed loop wherein said first strap and said second strap are configured to inhibit said condom from falling off of the user's penis during intercourse, said second mating member being positioned on said outer surface of said second strap, said second mating member being aligned with said secondary end of said second strap.

* * * * *